United States Patent [19]
Haindl

[11] Patent Number: 5,378,241
[45] Date of Patent: Jan. 3, 1995

[54] ANESTHESIA INSTRUMENT

[76] Inventor: Hans Haindl, Hauptstr. 39, 3015 Wennigsen 1, Germany

[21] Appl. No.: 81,791

[22] Filed: Jun. 23, 1993

[30] Foreign Application Priority Data

Jun. 24, 1992 [DE] Germany ............ 9208414[U]

[51] Int. Cl.$^6$ ............................................. A61M 5/178
[52] U.S. Cl. ..................................... 604/164; 604/264
[58] Field of Search ............... 604/158, 264, 266, 267, 604/164

[56] References Cited

U.S. PATENT DOCUMENTS

| | | | |
|---|---|---|---|
| 4,808,157 | 2/1989 | Coombs | 604/158 |
| 4,994,036 | 2/1991 | Biscoping | 604/158 |
| 5,053,046 | 10/1991 | Janese | 606/215 |
| 5,100,390 | 3/1992 | Lubeck et al. | 604/158 |
| 5,163,901 | 11/1992 | Eldor | 604/158 |
| 5,205,828 | 4/1993 | Kedem | 604/158 |

FOREIGN PATENT DOCUMENTS

| | | | |
|---|---|---|---|
| 67140 | 12/1982 | European Pat. Off. | ............ 604/264 |
| 3327585 | 2/1984 | Germany . | |
| 3830653 | 3/1990 | Germany . | |
| 3918431 | 7/1990 | Germany . | |
| 8900436 | 1/1989 | WIPO . | |

*Primary Examiner*—John G. Weiss
*Attorney, Agent, or Firm*—Allegretti & Witcoff, Ltd.

[57] ABSTRACT

An anesthesia instrument consists of a single lumen epidural cannula with a Touhy-type beveled aperture, an epidural catheter and a spinal cannula. The anesthesia instrument is characterized in that, the diameter or the cross-section of the epidural cannula is so dimensioned that, even with the epidural catheter positioned within the same, there is still sufficient space for the sliding through of a spinal cannula. In one form of the invention, marking means are provided to indicate at the proximal end of the epidural cannula, the position of the tip of the spinal cannula being inserted in the epidural cannula.

8 Claims, 4 Drawing Sheets

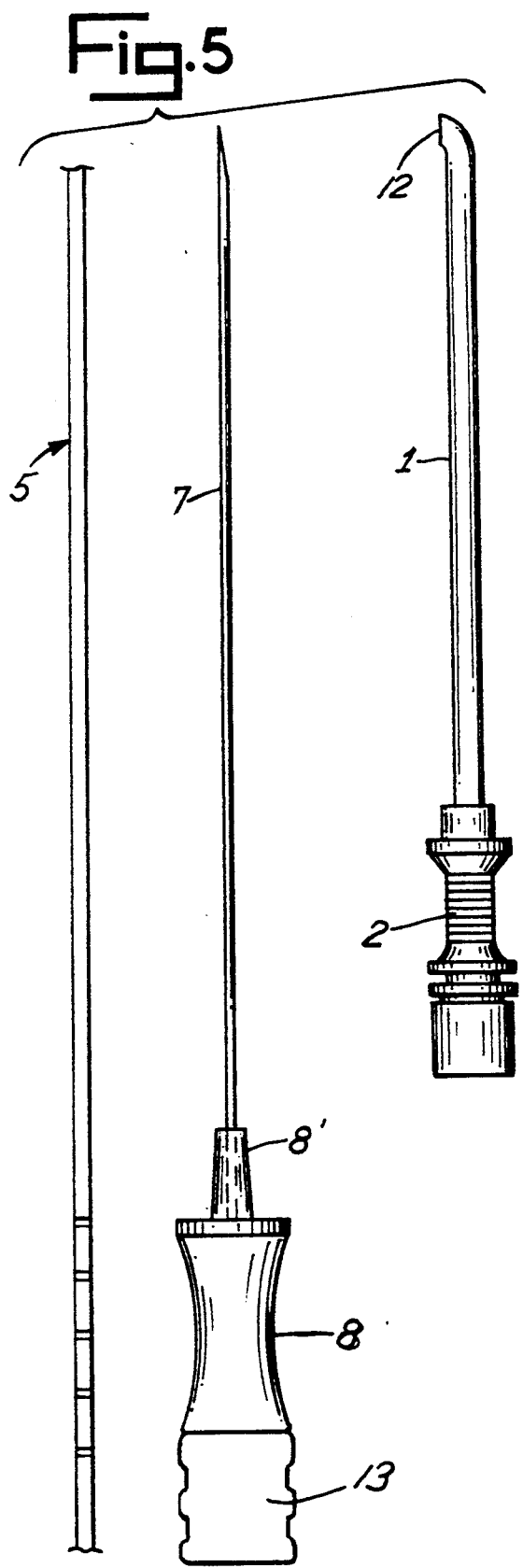
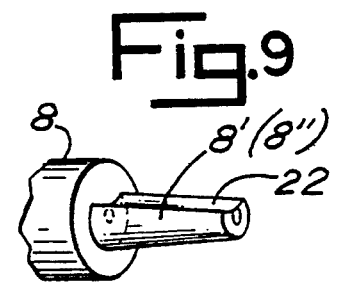
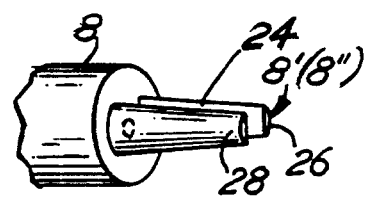
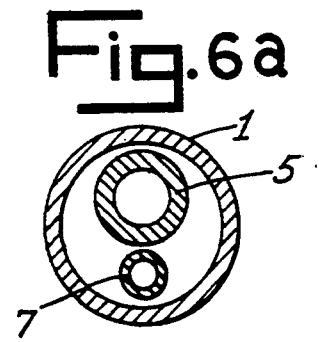
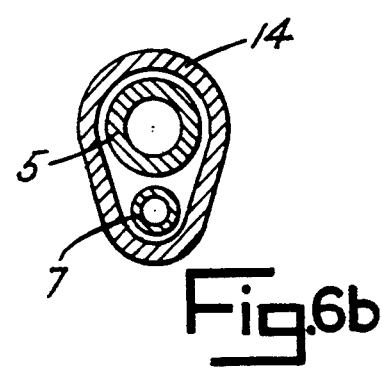

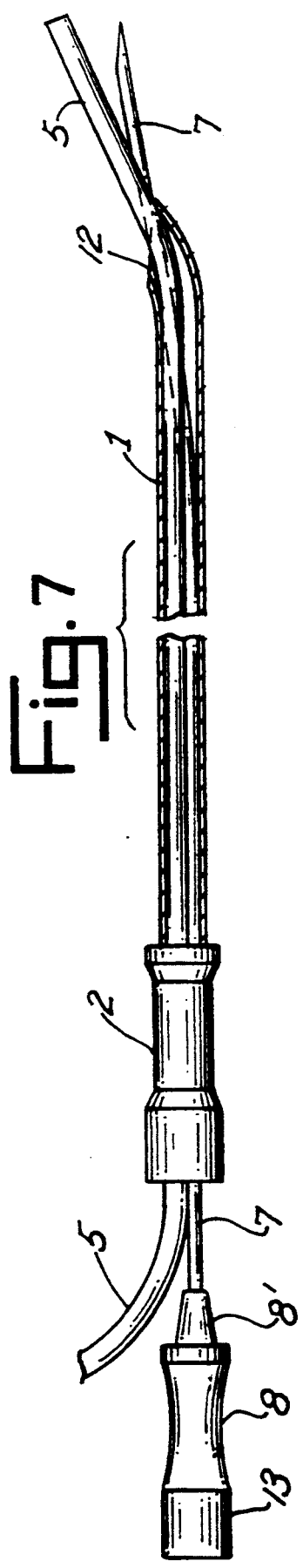
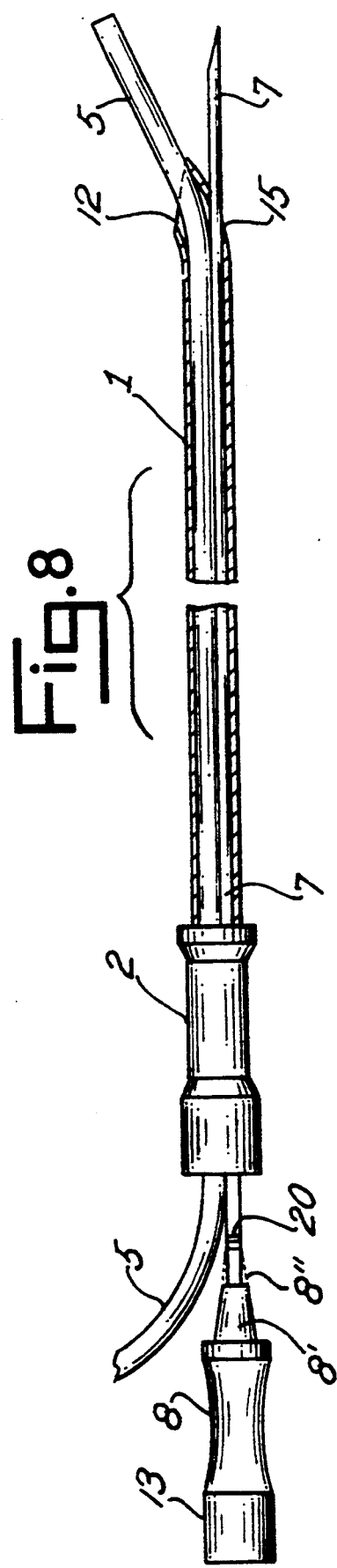

ANESTHESIA INSTRUMENT

BACKGROUND OF THE INVENTION

The invention relates to an anesthesia instrument consisting of an epidural cannula with an oblique aperture, an epidural catheter which can be guided through this cannula, and a spinal cannula, which is longer and thinner than the epidural cannula and which, with the catheter positioned in the epidural cannula, can still be slid through between the wall of the epidural cannula and the catheter.

PRIOR ART

Spinal anesthesia and epidural anesthesia are two processes of regional anesthesia which are essentially used in operations on the lower extremities and the pelvic organs. Both have their specific advantages and disadvantages, and it is obvious, given specific indications, to combine these. In this connection, there is already known, from the German patent disclosure document DE 39 22 406, an instrument in which the epidural cannula, the beveled end of which is bent laterally, has a second hole concentric with the cannula axis at its tip. In order to apply spinal anesthesia before the placing of the epidural catheter, the spinal cannula can be slid through this hole.

This instrument is useful but has, however, a disadvantage in the hands of the unskilled operator. The correct position of the epidural catheter is normally tested by means of a test dose of local anesthetic. The dose, which would correspond to a spinal anesthesia, is injected through the epidural catheter. If this is incorrectly positioned in a subdural position, as can often occur, then a spinal anesthesia results. An unknown subdural position can lead to life-threatening complications for the patients. In using the instrument mentioned, this monitoring is no longer possible since a spinal anesthesia already has been effected, even before introducing of the epidural catheter. This is one disadvantage of the instrument which is described in the German patent disclosure document number DE 39 22 406.

SUMMARY OF THE INVENTION

The anesthesia instrument of the invention permits the combination of both processes to be carried out in such a manner, that the position of the catheter can be tested first, and only then is the spinal anesthesia administered.

An anesthesia instrument which makes this possible is already known from the U.S. Pat. Nos. 4,808,157 and 4,958,901. These instruments have an epidural cannula with two lumina, through which the epidural catheter and the spinal cannula can be slid, in a manner completely independently of one another. These cannulas are very expensive to manufacture, and also, because of the two lumina, have a large diameter. Administering an epidural anesthesia using a large diameter cannula results in undesirable back pains.

In the invention described below, the desired characteristics are essentially attained by means of a suitable adjustment of the dimensions of the cannulas and of the catheter.

The inventive goal, in principle, can be attained by means of a single lumen large-caliber epidural cannula, such as size "16-G", for example, and sliding a thinner catheter, such as size "20-G", for example, therethrough. Enough space then remains between the cannula and the catheter in order, for example, to slide through a spinal cannula size "26-G".

In one particular form of the invention, the cannula tube has flattened side walls and provides enough space to accommodate both the catheter and the smaller diameter spinal cannula without the tube having to be too large in its overall cross section.

The sliding through of the spinal cannula under the beveled end of the cannula tube with the catheter positioned inside the tube is only possible by bending the spinal cannula with the tip of the epidural cannula. This could damage the spinal cannula tip. This can be avoided by providing a hole for the exit of the spinal cannula in the tip area of the epidural cannula, which is similar to that described in the German patent disclosure document DE 39 22 406, but with the difference that the hole in the wall of the cannula is, in this case, positioned not in a concentric manner but, rather, in an eccentric manner with respect to the axis of the epidural cannula.

In order to prevent the penetration of tissue into this additional hole, a mandrin or rod having the profile of the epidural cannula cross section may be used to seal the entire lumen of the cannula, including the additional hole.

BRIEF DESCRIPTION OF THE DRAWINGS

FIG. 5 is a composite plan view of the epidural cannula, the spinal cannula and the epidural catheter disassembled.

FIG. 6a is a cross sectional view through the lumen of the epidural cannula, with the spinal cannula and the epidural catheter disposed therein.

FIG. 6b is a view similar to 6a in which the epidural cannula has flattened side walls and is of smaller cross section spaced closely around the catheter and smaller diameter spinal cannula.

FIG. 7 is a side view of the anesthesia instrument showing the spinal cannula and the catheter extending through a lateral aperture in the beveled tip of the epidural cannula.

FIG. 8 is a view similar to FIG. 7 showing a modification of the invention in which the epidural cannula has a second separate aperture for the spinal cannula.

FIG. 9 is a perspective view of an attachment on the spinal cannula having a groove to accommodate the catheter.

FIG. 10 is a view similar to FIG. 9 of an alternate construction for the attachment having a pair of clamps which embrace the catheter.

DETAILED DESCRIPTION OF THE INVENTION

Figure 1:
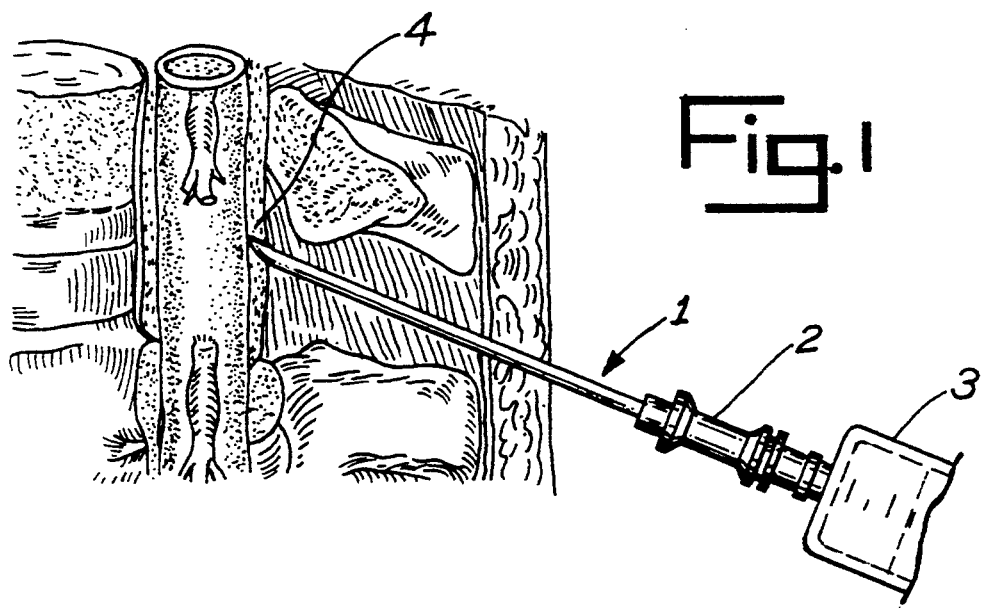
FIG. 1 is a side view of the anesthesia instrument of the invention with the epidural cannula inserted into the epidural space in the vertebral canal.
Figure 2:
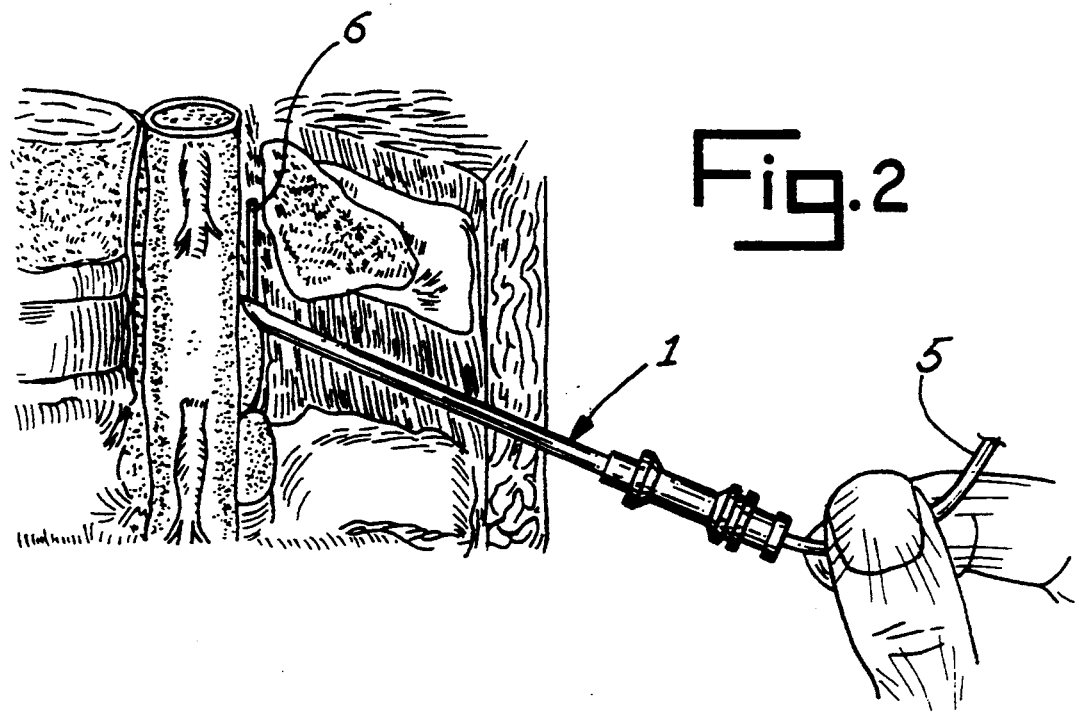
FIG. 2 is a view similar to FIG. 1 in which the syringe has been removed and the catheter has been positioned within the epidural cannula with the distal end extending into the epidural space.

FIGS. 1 to 4 depict the procedure for using the instrument of the invention. FIG. 1 depicts the single lumen epidural cannula 1, with the attachment 2 and the syringe 3, positioned with its tip in the epidural space 4 after puncturing in the conventional manner. After the puncture, the syringe is withdrawn and, as depicted in FIG. 2, the catheter 5 is slid in, until its tip 6 lies a few centimeters beyond the end of cannula 1 within the epidural space. After that, the usual test dose for monitoring the correct position is administered by means of the epidural catheter.

Figure 3:
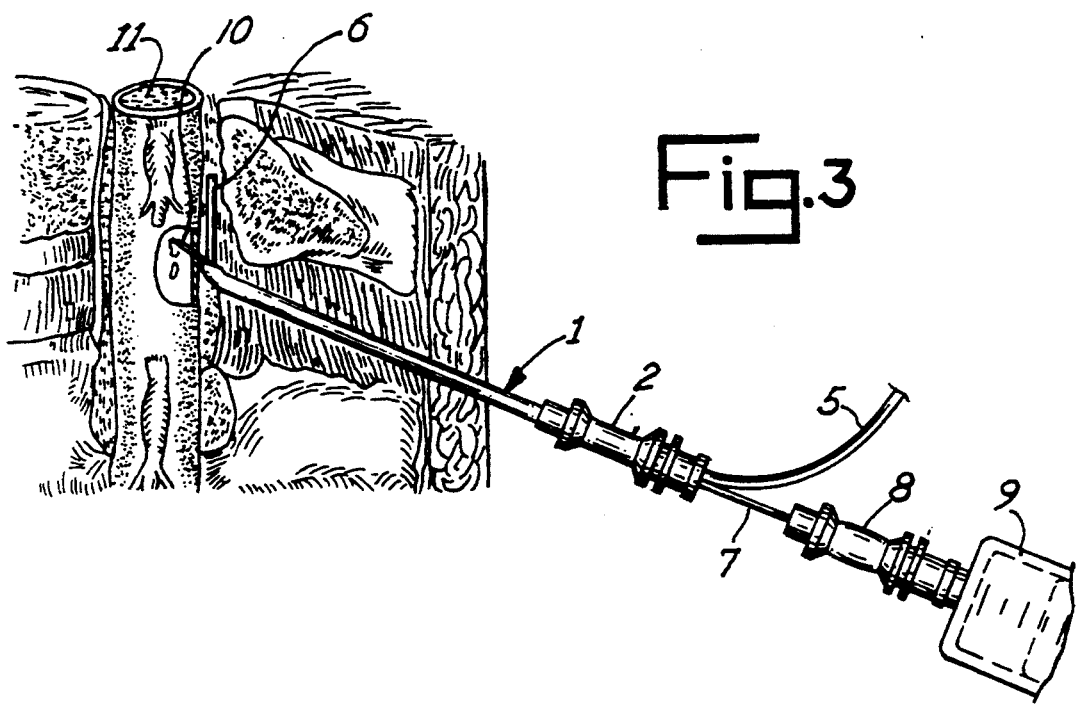
FIG. 3 is a view similar to FIG. 2 showing both the catheter and the spinal cannula inserted within the epidural cannula, the tip of the spinal cannula extending into the subdural space.
Figure 4:
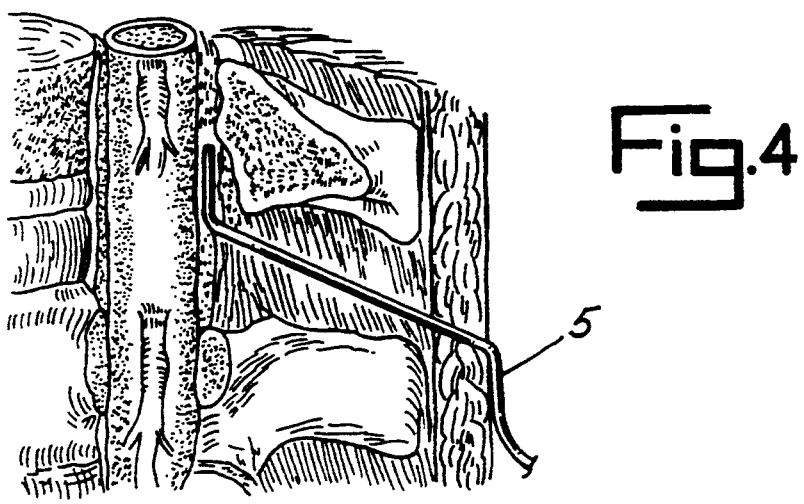
FIG. 4 is a view similar to FIG. 2 showing the proximal end of the catheter extending from the epidural space after removal of the epidural cannula and the spinal cannula.

As depicted in FIG. 3, a spinal cannula 7, also having an attachment 8 and a syringe 9, is inserted in the epidural cannula 1. As the spinal cannula tip 10 exits from the epidural cannula, it perforates the hard meninges layer and enters into the subdural space 11. The drug for the spinal anesthesia is injected into this space. The spinal cannula 7 then is removed, as well as the epidural cannula 1. The epidural catheter 5, as depicted in FIG. 4, remains in place.

FIG. 5 depicts the components of the instrument: the single lumen epidural cannula 1 with its hub or sleeve attachment 2 and the so-called "Touhy-type beveled aperture" 12 on the distal, turned end; the epidural catheter 5; and the spiral cannula 7 with attachment 8 on its proximal end. A Luer-type cone 8' extends from attachment 8 in order that the attachment 8 can be connected easily to the attachment 2 of the epidural cannula 1. After being inserted into the cannula 1, the spinal cannula 7 is sealed with a ram rod or mandrin, just like the epidural cannula 1. The attachment 13 of the rod can be seen on the cannula attachment 8. This rod (not shown) fills the distal opening and prevents closure by tissue.

FIGS. 6a and 6b depict the positions of the catheter and spinal cannula within the lumen of the epidural cannula. The epidural cannula 1 may take the form of a round tube having a single lumen in which the catheter 5 and the spinal cannula 7 are located next to one another as shown in FIG. 6a. Alternatively, the cannula 1 may take the form of a tube 14 with flattened side walls which is specifically manufactured for this purpose and which, by means of its non-circular shape, offers sufficient space for the catheter 5 and the spinal cannula 7, as shown in FIG. 6b, but without having the larger cross-section of the tube 1.

FIG. 7 shows the spinal cannula 7 inserted next to the catheter 5, in a conventional round epidural cannula 1. In this construction, the catheter and spinal cannula both exit through the aperture 12 of the Touhy-type beveled aperture in the laterally bent tip of cannula 1. The spinal cannula 7 is slightly pre-bent, or curved to bear against the wall of cannula 1 to minimize the danger of the tip cutting into the catheter 5.

FIG. 8 depicts another arrangement, in which the slightly pre-bent spinal cannula 7 exits from a hole 15 in the curved wall of the tip of cannula 1 below the Touhy-type beveled aperture 12. The hole 15 is eccentric with respect to the axis of the lumen of cannula 1. In this arrangement, the spinal cannula need not be curved. The arrangement with the additional hole 15 is particularly useful with the non-circular epidural cannula tube 14 as shown in FIG. 6b.

The slightly pre-curved spinal cannula can be used advantageously with the cannula 1 shown in FIG. 8 when properly oriented toward the wall opposite the catheter 5 because the curvature ensures that its tip always proceeds along the wall of the cannula and exits the hole 15. This arrangement also has the advantage that the instrument can also be used in the procedure disclosed in application number DE 39 22 406 where the spinal anesthesia is administered before sliding the catheter through cannula 1.

In order to prevent the penetration of tissue into the hole 15 prior to injection, a profiled rod having the configuration of the cannula 1 is provided to seal temporarily the entire lumen of the cannula, as well as the hole 15. The attachment 13 for the rod is shown in FIG. 8.

In order to determine in a simple manner whether the spinal cannula 7 has reached the tip of the epidural cannula 1, a marking ring 20 can be provided on the spinal cannula, as shown in FIG. 8. Alternatively, a Luer-type cone 8' may be provided on the attachment 8 of the spinal cannula 7. The cone 8' may be lengthened by adding an extension 8" as shown in FIG. 8. The alignment of the marking 20 or of the extension 8" with the face of the attachment 2 of the epidural cannula indicates that the tip of the spinal cannula 7 has reached the tip of the epidural cannula.

The attachment 8 and/or the Luer-type cone 8' of the spinal cannula 7 can, as is schematically depicted in FIG. 9, be equipped, on one side, with an indentation or a groove 22 extending in the direction of the cannula, in order to accommodate the epidural catheter 5. This facilitates insertion of the attachment 8 into the attachment 2 of the epidural cannula 1 even when the epidural catheter 5 has already been slid into place.

I claim:

1. An anesthesia instrument comprising
    a single lumen epidural cannula terminating in a beveled aperture,
    an epidural catheter adapted for insertion within said lumen,
    a spinal cannula having a sharp tip, adapted for insertion within said lumen adjacent said epidural catheter,
    said spinal cannula being slightly pre-bent to definitively position said tip within said lumen to prevent the tip from cutting into said epidural cannula when said spinal cannula is inserted in said lumen after said epidural catheter is positioned therein.

2. An anesthesia instrument having proximal and distal ends comprising
    a single lumen epidural cannula terminating in a beveled aperture,
    an epidural catheter adapted for insertion within said lumen,
    a spinal cannula adapted for insertion within said lumen adjacent said epidural catheter, and
    an attachment on the proximal end of said spinal cannula, said attachment having a groove in its external surface to accommodate said epidural catheter.

3. The anesthesia instrument of claim 2 in which said groove is disposed in a Luer-type cone comprising part of the attachment.

4. The anesthesia instrument of claim 2 in which said attachment has an entrance face and said spinal cannula carries a marking which indicates that the tip of said spinal cannula has reached said beveled aperture when said marking is aligned with said entrance face.

5. The anesthesia instrument of claim 2 in which said attachment has an entrance face and said spinal cannula has a Luer-type cone surrounding it and so positioned along its length that when said spinal cannula is inserted into said epidural cannula and said cone reaches said entrance face, the tip of said spinal cannula has reached said beveled aperture.

6. An anesthesia instrument having proximal and distal ends comprising
   a single lumen epidural cannula terminating in a beveled aperture,
   an epidural catheter adapted for insertion in said lumen,
   a spinal cannula adapted for insertion in said lumen adjacent said epidural catheter, and
   an attachment on the proximal end of said instrument comprising a Luer-type cone split along its longitudinal axis to provide a slot for receiving said epidural catheter.

7. An anesthesia instrument comprising
   a single lumen epidural cannula terminating in a beveled aperture,
   an epidural catheter adapted for insertion in said lumen,
   a spinal cannula adapted for insertion in said lumen adjacent said epidural catheter,
   said epidural cannula having
      a curved tip including said beveled aperture,
      a hole opposite said beveled aperture, eccentric with respect to the axis of said epidural cannula, through which said spinal cannula can exit,
      flattened side walls which join a first curved wall with a second curved wall of smaller radius than that of said first curved wall, said first curved wall extending to said beveled aperture, and said second curved wall extending to said hole, and
   said epidural catheter, when inserted in said lumen, being closely spaced from said first curved wall and said spinal cannula, when inserted in said lumen being closely spaced from said second curved wall.

8. The anesthesia instrument of claim 7 in which the diameter of said spinal cannula is smaller than the diameter of said epidural catheter.

* * * * *